United States Patent
Johnson et al.

(10) Patent No.: US 7,960,431 B2
(45) Date of Patent: Jun. 14, 2011

(54) THIOPHENYL PROSTAGLANDIN DERIVATIVES FOR TREATING GLAUCOMA AND OCULAR HYPERTENSION

(75) Inventors: Brent A. Johnson, Ladera Ranch, CA (US); David W. Old, Irvine, CA (US); Yariv Donde, Dana Point, CA (US); Robert M. Burk, Laguna Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 12/525,335

(22) PCT Filed: Jan. 30, 2008

(86) PCT No.: PCT/US2008/052375
§ 371 (c)(1),
(2), (4) Date: Mar. 23, 2010

(87) PCT Pub. No.: WO2008/094958
PCT Pub. Date: Aug. 7, 2008

(65) Prior Publication Data
US 2010/0173981 A1    Jul. 8, 2010

Related U.S. Application Data

(60) Provisional application No. 60/887,759, filed on Feb. 1, 2007.

(51) Int. Cl.
*A01N 43/06* (2006.01)
(52) U.S. Cl. .......................................... 514/448; 549/71
(58) Field of Classification Search ............... 514/231.5, 514/448; 549/71; 544/146
See application file for complete search history.

(56) References Cited

U.S. PATENT DOCUMENTS

| 6,586,463 B2 * | 7/2003 | deLong et al. ................. 514/443 |
| 2005/0209337 A1 | 9/2005 | Gutman et al. |

FOREIGN PATENT DOCUMENTS

| WO | WO 00/51977 | * | 2/2000 |
| WO | WO02096868 | | 12/2002 |
| WO | WO 2006/022966 | * | 3/2006 |

OTHER PUBLICATIONS

U.S. Appl. No. 60/805,285, filed Jun. 20, 2006, David W. Old, et al.
Francis A. Carey, Organic Chemistry, New York: McGraw-Hill Book Company 1987, p. 63.

Smith and March, March's Advanced Organic Chemistry, Fifth Ed., New York: Wiley-Interscience, 2001, pp. 1195-1196.

* cited by examiner

*Primary Examiner* — Yong Chu
*Assistant Examiner* — Valerie Rodriguez-Garcia
(74) *Attorney, Agent, or Firm* — Kevin J. Forrestal; John E. Wurst; Doina G. Ene

(57) ABSTRACT

Disclosed herein is a compound according to one of the formulas or a pharmaceutically acceptable salt thereof, medicaments for the treatment of glaucoma or ocular hypertension and compositions related thereto, as further elaborated herein.

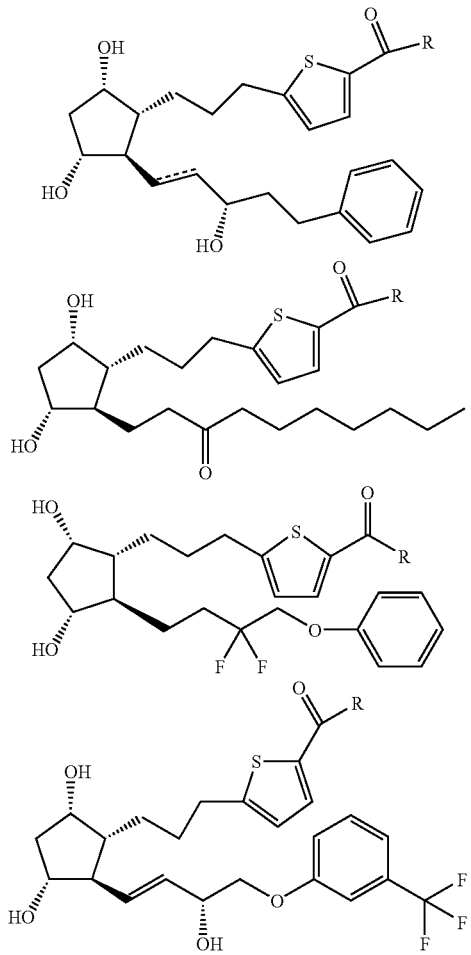

19 Claims, No Drawings

THIOPHENYL PROSTAGLANDIN DERIVATIVES FOR TREATING GLAUCOMA AND OCULAR HYPERTENSION

CROSS REFERENCE TO RELATED APPLICATIONS

This is a national stage application under 35 U.S.C. 371 of PCT patent application PCT/US2008/052375, filed on Jan. 30, 2008, which claims the benefit of U.S. Provisional Patent Application 60/887,759, filed Feb. 1, 2007, each of which is hereby incorporated by reference in its entirety.

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

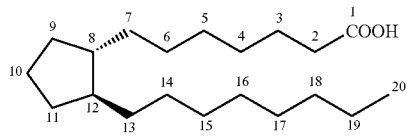

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}(PGF_2\beta)$].

Disclosed herein is a compound according to one of the formulas

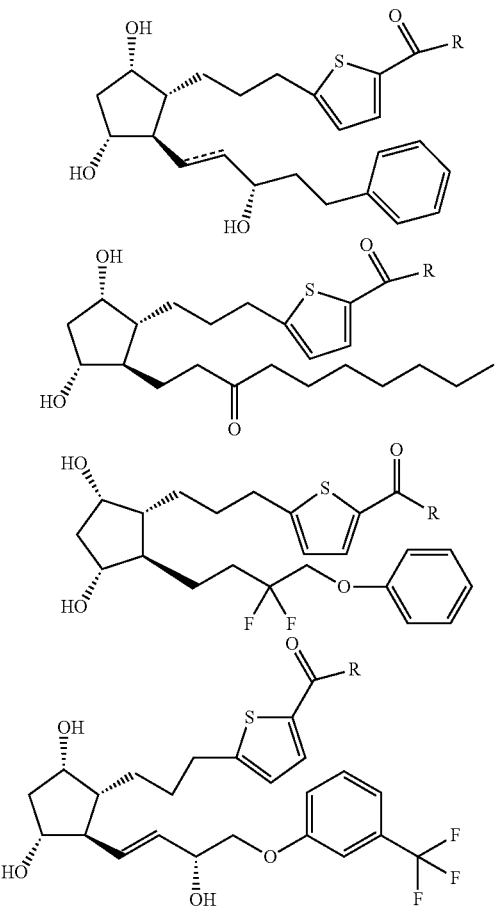

or a pharmaceutically acceptable salt thereof
wherein a dashed line represents the presence or absence of a bond;
wherein R is OH, $OR^1$, or $NHR^1$, and
$R^1$ is $C_{1-4}$ alkyl.

$C_{1-4}$alkyl is a saturated hydrocarbon having from 1 to 4 carbons, e.g. methyl, ethyl, isopropyl, n-propyl, butyl isomers, cyclopropyl, cyclobutyl, and the like.

In one embodiment, R is OH.
In another embodiment, $R^1$ is isopropyl.
In another embodiment, $R^1$ is $HNHCH_2CH_3$.

A pharmaceutically acceptable salt is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt. Examples of useful salts include, but are not limited to, sodium salts, potassium salts, calcium salts, ammonium salts and the like.

A person of ordinary skill in the art understands the meaning of the stereochemistry associated with the hatched wedge/solid wedge structural features. For example, an introductory organic chemistry textbook (Francis A. Carey, Organic Chemistry, New York: McGraw-Hill Book Company 1987, p. 63) states "a wedge indicates a bond coming from the plane of the paper toward the viewer" and the hatched wedge "represents a bond receding from the viewer."

For the purposes of this disclosure, "treat," "treating," or "treatment" refer to the use of a compound, composition, therapeutically active agent, or drug in the diagnosis, cure, mitigation, treatment, or prevention of disease or other undesirable condition.

One embodiment is a composition comprising a compound disclosed herein, wherein said composition is a liquid which is ophthalmically acceptable.

Another embodiment is use of a compound disclosed herein in the manufacture of a medicament for the treatment of glaucoma or ocular hypertension in a mammal.

Another embodiment is a medicament comprising a compound disclosed herein, wherein said composition is a liquid which is ophthalmically acceptable.

Another embodiment is a method comprising administering a compound disclosed herein to a mammal for the treatment of glaucoma or ocular hypertension.

Another embodiment is a kit comprising a composition comprising compound disclosed herein, a container, and instructions for administration of said composition to a mammal for the treatment of glaucoma or ocular hypertension.

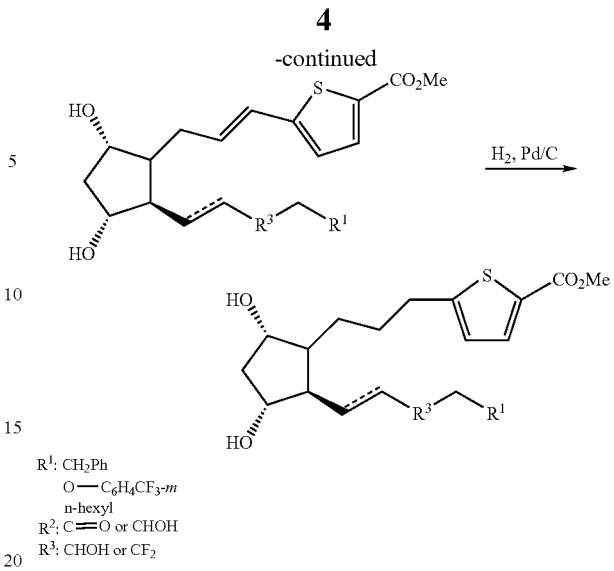

$R^1$: $CH_2Ph$
    O—$C_6H_4CF_3$-$m$
    n-hexyl
$R^2$: C═O or CHOH
$R^3$: CHOH or $CF_2$ A person of ordinary skill in the art recognizes that are many potential methods to prepare these compounds. For example, WO02096868 and US20050209337 disclose methods that can be adapted to prepare these compounds (Scheme 1). A thienyl containing Wittig reagent (A) can be substituted for the linear Wittig reagent of those reference to yield the thienyl containing alpha chain. The resulting thienyl propenyl thienyl alpha chain can then be hydrogenated to yield the desired alpha chain. The terminal ester may be transesterified, saponified or converted to any desired amide. Compound A may also be substituted with a compound such as compound B, and the alpha chain can be attached as described in U.S. Provisional Patent Application No. 60/805,285, filed on Jul. 20, 2006.

Synthetic Methods

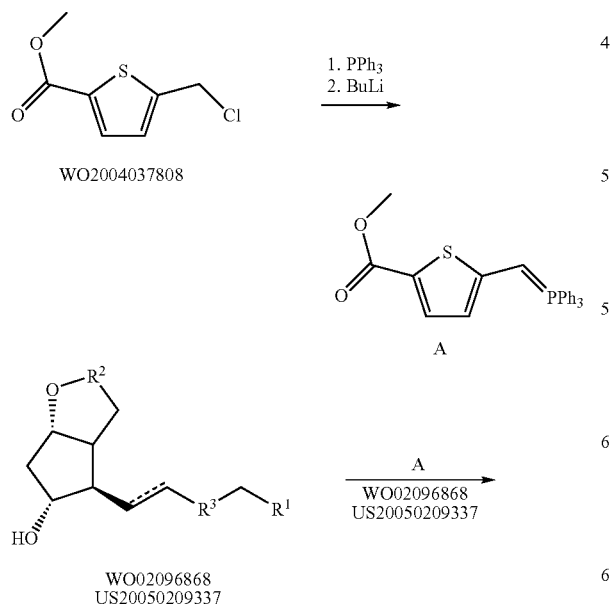

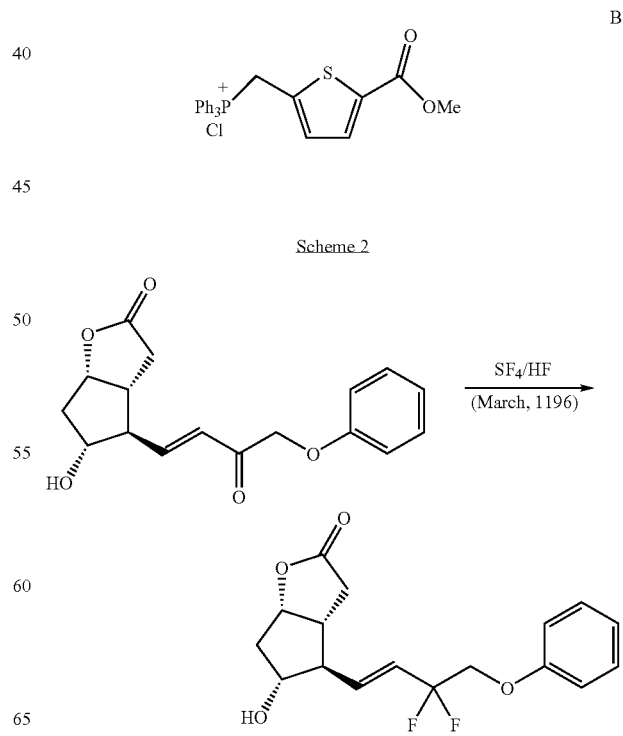

Compounds having $CF_2$ for $R^3$ may be prepared by reaction with SF4/HF or an equivalent reagent as described in Smith and March, March's Advanced Organic Chemistry, Fifth Ed., New York: Wiley-Interscience, 2001, pp. 1195-1196. Other methods may also be used.

Formulation Methods

A liquid which is ophthalmically acceptable is formulated such that it can be administered topically to the eye. The comfort should be maximized as much as feasible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used to achieve an ophthalmically acceptable pH. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 0-10 |
| buffer | 0.01-10 |
| pH adjustor | q.s. pH 4.5-7.5 |
| antioxidant | as needed |
| surfactant | as needed |
| purified water | as needed to make 100% |

The actual dose of the active compounds depends on the specific compound, and on the condition to be treated; the selection of the appropriate dose is well within the knowledge of the skilled artisan.

TREATMENT EXAMPLES

The following are hypothetical examples demonstrating how a person may be treated with the compounds disclosed herein.

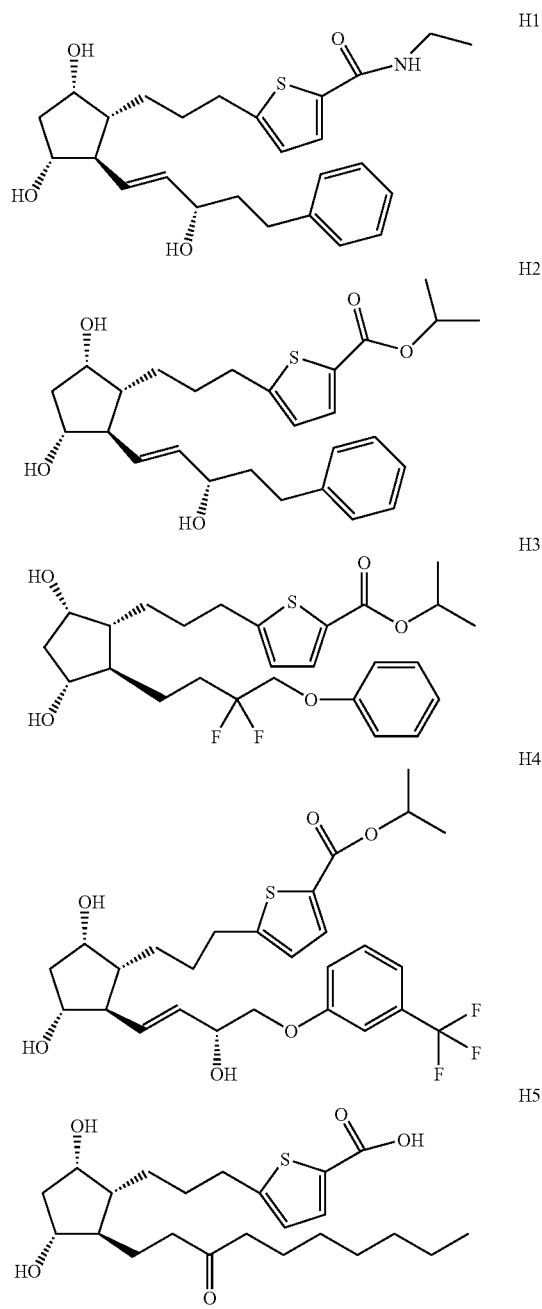

An aqueous liquid containing 0.1% of H1 is given topically to the eye of a person suffering from elevated intraocular pressure. A few hours after administration, the person's intraocular pressure is reduced. The drop is administered twice a day, and pressure remains low for as long as the treatment is continued.

An aqueous liquid containing 0.1% of H2 is given topically to the eye of a person suffering from elevated intraocular pressure. A few hours after administration, the person's intraocular pressure is reduced. The drop is administered twice a day, and pressure remains low for as long as the treatment is continued.

An aqueous liquid containing 0.1% of H3 is given topically to the eye of a person suffering from elevated intraocular pressure. A few hours after administration, the person's intraocular pressure is reduced. The drop is administered twice a day, and pressure remains low for as long as the treatment is continued.

An aqueous liquid containing 0.1% of H4 is given topically to the eye of a person suffering from elevated intraocular pressure. A few hours after administration, the person's intraocular pressure is reduced. The drop is administered twice a day, and pressure remains low for as long as the treatment is continued.

An aqueous liquid containing 0.1% of H5 is given topically to the eye of a person suffering from elevated intraocular pressure. A few hours after administration, the person's intraocular pressure is reduced. The drop is administered twice a day, and pressure remains low for as long as the treatment is continued.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the claims.

What is claimed is:

1. A compound according to one of the formulas or a pharmaceutically acceptable salt thereof
wherein a dashed line represents the presence or absence of a bond;
wherein R is OH, $OR^1$, or $NHR^1$, and
$R^1$ is $C_{1-4}$ alkyl.

2. The compound of claim 1 of the formula or a pharmaceutically acceptable salt thereof.

3. The compound of claim 2 wherein R is OH, or a pharmaceutically acceptable salt thereof.

4. The compound of claim 2 wherein $R^1$ is isopropyl.

5. The compound of claim 1 of the formula or a pharmaceutically acceptable salt thereof.

6. The compound of claim 5 wherein R is OH, or a pharmaceutically acceptable salt thereof.

7. The compound of claim 5 wherein R is $NHCH_2CH_3$.

8. The compound of claim 1 of the formula

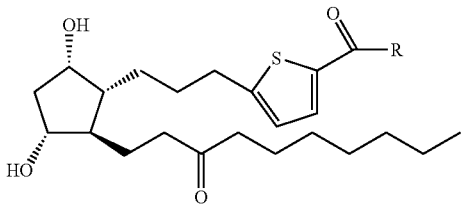

or a pharmaceutically acceptable salt thereof.

9. The compound of claim 8 wherein R is OH, or a pharmaceutically acceptable salt thereof.

10. The compound of claim 8 wherein $R^1$ is isopropyl.

11. The compound of claim 1 of the formula

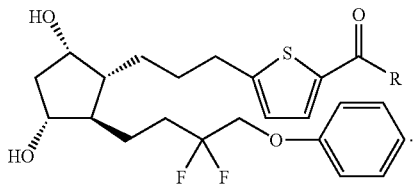

12. The compound of claim 11 wherein R is OH, or a pharmaceutically acceptable salt thereof.

13. The compound of claim 11 wherein $R^1$ is isopropyl.

14. The compound of claim 1 of the formula

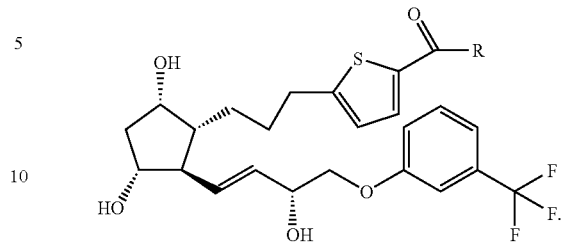

15. The compound of claim 14 wherein R is OH, or a pharmaceutically acceptable salt thereof.

16. The compound of claim 14 wherein $R^1$ is isopropyl.

17. A method of treating glaucoma or ocular hypertension comprising administering a compound according to claim 1 wherein said treating consists of treating, mitigating or curing an established condition.

18. A composition comprising a compound according to claim 1, wherein said composition is an aqueous liquid suitable for topical ophthalmic administration.

19. A kit comprising a composition of claim 18, a package for dispensing drops of the liquid, and directions indicating use of the composition topically for treating glaucoma or ocular hypertension.

* * * * *